United States Patent
Teshigawara

(10) Patent No.: US 10,436,915 B2
(45) Date of Patent: Oct. 8, 2019

(54) MEDICAL IMAGE DIAGNOSIS APPARATUS

(71) Applicant: Canon Medical Systems Corporation, Otawara-shi (JP)

(72) Inventor: Manabu Teshigawara, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 0 days.

(21) Appl. No.: 16/133,796

(22) Filed: Sep. 18, 2018

(65) Prior Publication Data

US 2019/0086557 A1    Mar. 21, 2019

(30) Foreign Application Priority Data

Sep. 20, 2017 (JP) .................. 2017-180423
Sep. 13, 2018 (JP) .................. 2018-171262

(51) Int. Cl.
| | |
|---|---|
| *G01T 1/164* | (2006.01) |
| *A61B 6/03* | (2006.01) |
| *G01T 1/20* | (2006.01) |
| *G01T 1/40* | (2006.01) |
| *G01T 1/24* | (2006.01) |

(52) U.S. Cl.
CPC .......... *G01T 1/1642* (2013.01); *A61B 6/037* (2013.01); *G01T 1/2018* (2013.01); *G01T 1/40* (2013.01); *A61B 6/032* (2013.01); *G01T 1/2002* (2013.01); *G01T 1/249* (2013.01)

(58) Field of Classification Search
CPC ..... G01T 1/1644; G01T 1/1647; G01T 1/202; G01T 1/1642; G01T 1/2002; G01T 1/249; G01T 1/40; A61B 6/425; A61B 6/508; A61B 6/032; A61B 6/037
See application file for complete search history.

(56) References Cited

U.S. PATENT DOCUMENTS

| | | | |
|---|---|---|---|
| 2004/0227091 A1 | 11/2004 | Leblanc et al. | |
| 2009/0097613 A1* | 4/2009 | Tonami | G01T 1/1644 378/19 |
| 2016/0299240 A1 | 10/2016 | Cho et al. | |
| 2016/0299246 A1 | 10/2016 | Minto et al. | |

FOREIGN PATENT DOCUMENTS

| | | |
|---|---|---|
| JP | 2009-281816 | 12/2009 |
| JP | 2010-249534 | 11/2010 |
| JP | 2017-215194 | 12/2017 |

* cited by examiner

*Primary Examiner* — David P Porta
*Assistant Examiner* — Fani Boosalis
(74) *Attorney, Agent, or Firm* — Oblon, McClelland, Maier & Neustadt, L.L.P.

(57) ABSTRACT

A medical image diagnosis apparatus of an embodiment includes a self-radioactive scintillator constituted of a single crystal; plural photon detectors that are arranged at various positions in the scintillator, and that output an electrical signal according to a quantity of radiation radiated from the scintillator; and calibration circuitry configured to calibrate an electrical signal output from each of the photon detectors such that calculation results based on the electrical signal output from each of the photon detectors are same among the photon detectors.

9 Claims, 7 Drawing Sheets

| MODULE ID | SPATIAL POSITION (P) | ENERGY VALUE (E) | DETECTION TIME (T) |
|---|---|---|---|
| D1 | P11 | E11 | T11 |
| | P12 | E12 | T12 |
| | P13 | E13 | T13 |
| | ⋮ | ⋮ | ⋮ |

| MODULE ID | SPATIAL POSITION (P) | ENERGY VALUE (E) | DETECTION TIME (T) |
|---|---|---|---|
| D2 | P21 | E21 | T21 |
| | P22 | E22 | T22 |
| | P23 | E23 | T23 |
| | ⋮ | ⋮ | ⋮ |

| MODULE ID | SPATIAL POSITION (P) | ENERGY VALUE (E) | DETECTION TIME (T) |
|---|---|---|---|
| D3 | P31 | E31 | T31 |
| | P32 | E32 | T32 |
| | P33 | E33 | T33 |
| | ⋮ | ⋮ | ⋮ |

| COINCIDENCE NO. | SPATIAL POSITION (P) | ENERGY VALUE (E) | DETECTION TIME (T) | SPATIAL POSITION (P) | ENERGY VALUE (E) | DETECTION TIME (T) |
|---|---|---|---|---|---|---|
| 1 | P11 | E11 | T11 | | | |
| 2 | P12 | E12 | T12 | P22 | E22 | T22 |
| 3 | P13 | E13 | T13 | P32 | E32 | T32 |
| ... | ... | ... | ... | P33 | E33 | T33 |
| | | | | ... | ... | ... |

MEDICAL IMAGE DIAGNOSIS APPARATUS

CROSS-REFERENCE TO RELATED APPLICATIONS

This application is based upon and claims the benefit of priority from Japanese Patent Application No. 2017-180423, filed on Sep. 20, 2017; and Japanese Patent Application No. 2018-171262, filed on Sep. 13, 2018, the entire contents of which are incorporated herein by reference.

FIELD

An embodiment described herein relates generally to a medical image diagnosis apparatus.

BACKGROUND

Generally, gamma detectors (hereinafter, "detector") in a positron emission computed tomography (PET) apparatus receive, by a photomultiplier tube, scintillation light that is (scintillation photons, optical photons) emitted when a gamma ray radiated from a subject enters a scintillator, and convert into an electrical signal.

In conventional detectors in the PET apparatus, many of scintillator crystals, a single unit of which is a scintillator crystal, for example, in the size of several millimeters in length, several millimeters in width, and several tens of millimeters in height (thickness), assembled in an array are used. Moreover, a reflective material is arranged between the scintillator crystals to prevent scintillation light generated inside one scintillator crystal from leaking to adjacent scintillator crystals (crosstalk). Therefore, the conventional detectors discretely identify a scintillator crystal in which a scintillation event occurs.

This identification is based on a precondition that output powers of the detector with respect to reception of a specific number of scintillation photons have been known. The PET apparatuses generally perform processing of adjusting the output power by an amplifier, or data processing of correcting the power by software means in a later stage based on this known information.

BRIEF DESCRIPTION OF THE DRAWINGS

FIG. 6 is a diagram for explaining a time-series list of simultaneous count data in the first embodiment;

DETAILED DESCRIPTION

Figure 1:
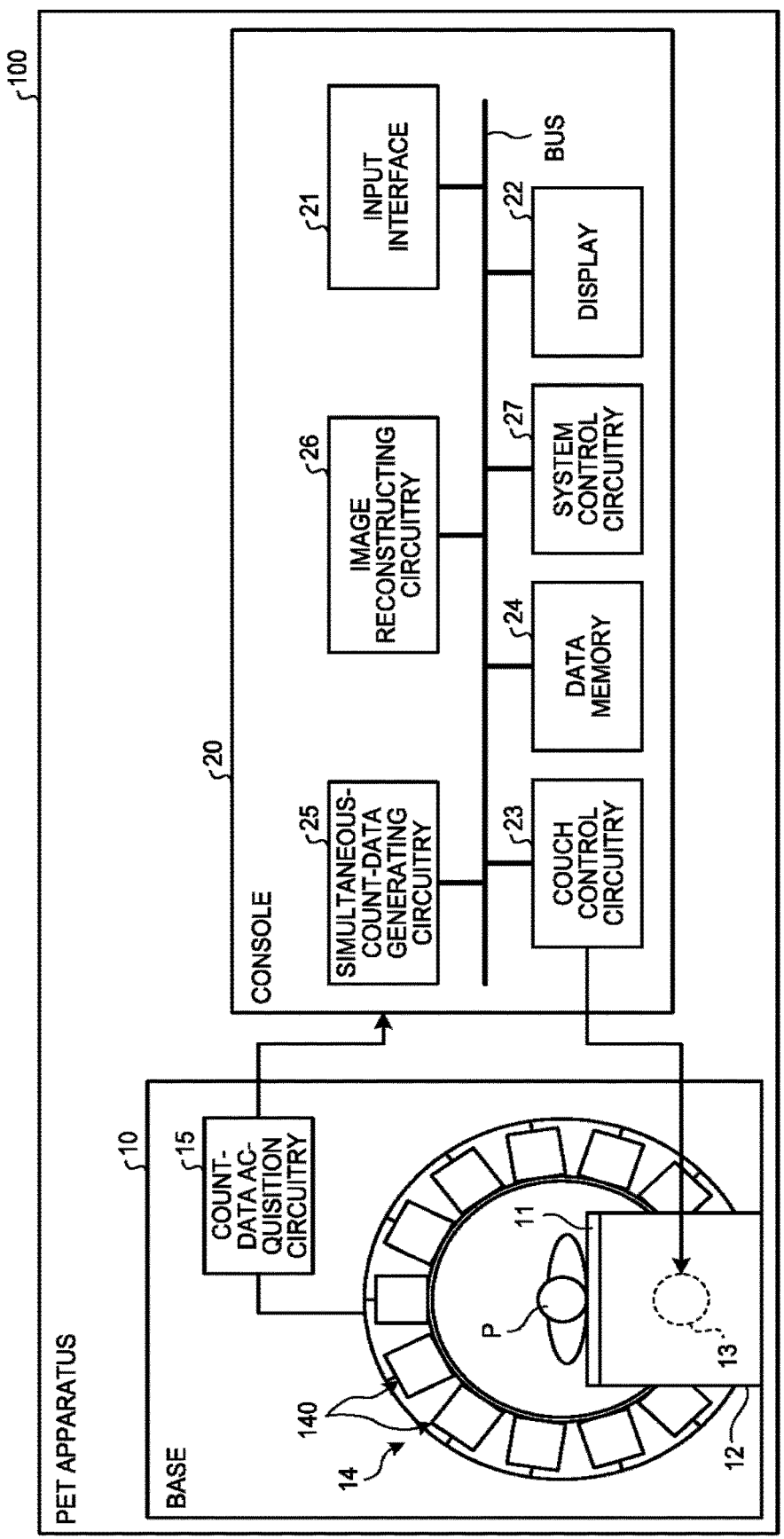
FIG. 1 is a block diagram showing a configuration of a PET apparatus according to a first embodiment.

A medical image diagnosis apparatus comprises a self-radioactive scintillator, a plurality of photon detectors, and calibration circuitry. The self-radioactive scintillator is constituted of a single crystal. The plurality of photon detectors are arranged at a plurality of different positions in the scintillator, and output an electrical signal according to a quantity of radiation radiated from the scintillator. The calibration circuitry configured to calibrate an electrical signal output from each of the photon detectors such that calculation results based on the electrical signal output from each of the photon detectors are same among the photon detectors.

The medical image diagnosis apparatus according to an embodiment is explained below, referring to the drawings. In the following, a case in which the medical image diagnosis apparatus is a PET apparatus is explained as an example. Embodiments are not limited to the embodiment below. Moreover, what is described in an embodiment is also applicable to other embodiments in principle.

FIG. 1 is a block diagram showing a configuration of a PET apparatus 100 according to a first embodiment. As shown in FIG. 1, the PET apparatus 100 according to the first embodiment includes a base 10 and a console 20.

The base 10 detects a pair of annihilation gamma rays that are emitted from a positron inside a subject P by a detector that is arranged to surround a periphery of the subject P in a ring shape, generates count data from output signals of the detector, and acquires the data. As shown in FIG. 1, the base 10 includes a tabletop 11, a couch 12, a couch driver 13, a detector 14, and count-data acquisition circuitry 15. The base 10 has a hollow to be an imaging opening as shown in FIG. 1.

The tabletop 11 is a bed on which the subject P is placed, and is arranged on the couch 12. The couch driver 13 moves the tabletop 11 under control of a couch control circuitry 23 described later. For example, the couch driver 13 moves the subject P into the imaging opening of the base 10 by moving the tabletop 11.

The detector 14 detects an annihilation gamma ray emitted from a positron inside the subject P. For example, the detector 14 has plural detector modules 140 that are arranged to surround a periphery of the subject P in a ring shape. Although the detector modules 140 are arranged in a tangential direction of circumference of the detector 14 in the example of FIG. 1, the detector modules 140 can be arranged in a body axis direction.

Figure 2:
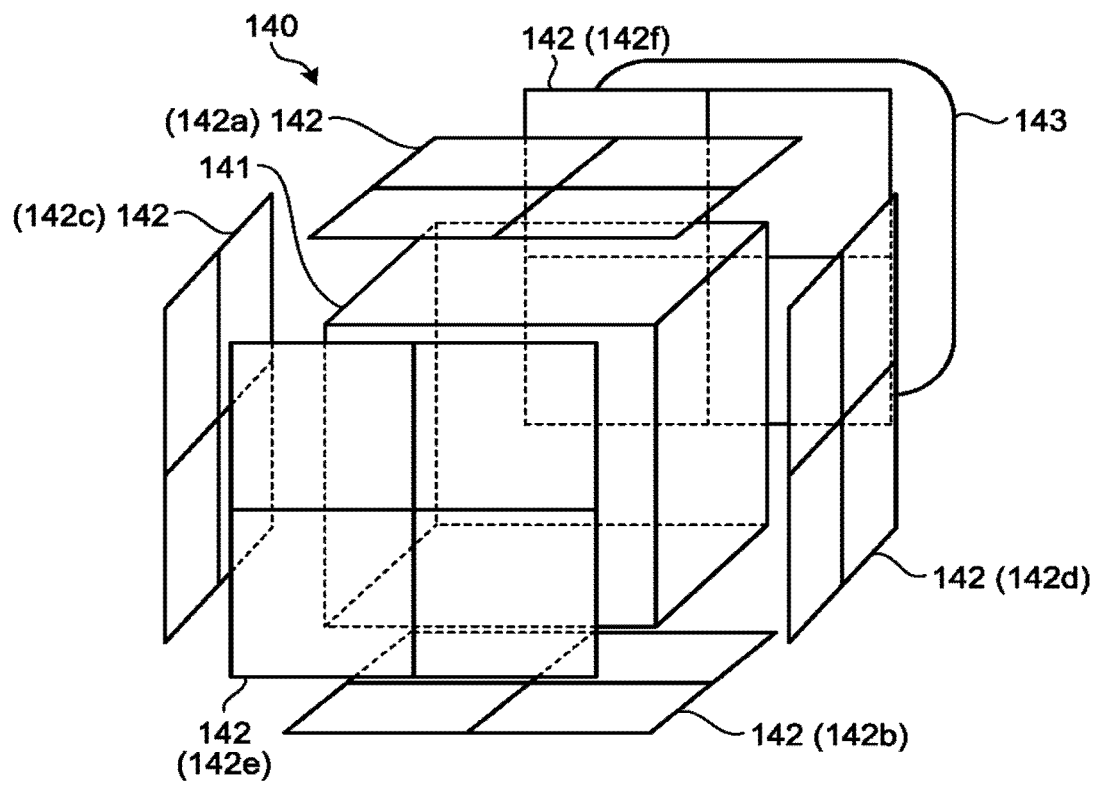
FIG. 2 is a diagram for explaining a detector module according to the first embodiment.

FIG. 2 is a diagram for explaining the detector module 140 according to the first embodiment. As shown in FIG. 2, the detector module 140 is an Anger detector by photon counting, and includes a scintillator 141, plural silicon photomultiplier (SiPM) panel 142, and count-data calculating circuitry 143. When each of the SiPM panels 142 is distinguished, different symbols are assigned as an SiPM panel 142a, an SiPM panel 142b, an SiPM panel 142c, an SiPM panel 142d, an SiPM panel 142e, and an SiPM panel 142f for convenience in explanation.

The scintillator 141 has a monolithic structure. "Monolithic" herein means being formed in one unit or one piece of plate. That is, the scintillator 141 is structured with a single crystal. Therefore, in the monolithically structured scintillator 141, not multiple scintillator crystals, a single unit of which is a scintillator crystal, assembled in an array, but each scintillator crystal is used as it is, unified, without being divided. Accordingly, no reflective materials are arranged in between in the scintillator 141.

Furthermore, the scintillator 141 is a hexahedron as shown in FIG. 2. Although FIG. 2 shows the scintillator 141 in a cubic shape, the scintillator 141 can have a rectangular parallelepiped shape. Moreover, the scintillator 141 is constituted of, for example, a scintillator crystal of an Lu family, such as lutetium yttrium oxyorthosilicate (LYSO), lutetium oxyorthosilicate (LSO), and luteritum gadolinium oxyorthosilicate (LGSO). Lu-family scintillator crystals include a radioactive isotope, Lu-176 that emits photons of 88 kiloelectron volts (keV), 201 keV, 306 keV, and 400 keV.

The scintillator 141 converts, for example, an incident annihilation gamma ray that has been emitted from a positron inside the subject P into scintillation light (scintillation photons, optical photons). That is, the scintillator 141 is structured monolithically, and converts gamma rays into scintillation light.

The SiPM panels 142 are arranged at various positions in the scintillator 141, and detects the scintillation light obtained by conversion by the scintillator 141 to generate an electrical signal. The SiPM panels 142 are arranged on at least two faces of the scintillator 141.

For example, the SiPM panels 142 are arranged on respective six faces of the scintillator 141 as shown in FIG. 2. In other words, all of six faces of the monolithically structured scintillator 141 are covered with the SiPM panels 142 in the example shown in FIG. 2. Note that the number of faces of the scintillator 141 to be covered can be less than six, or a part of the entire surface can be covered. Furthermore, as a rate of a surface of the scintillator covered with the SiPM panels 142 increases, a signal-to-noise ratio (S/N) of an output signal improves.

The SiPM panel 142 can be first formed on a substrate and then arranged on the scintillator 141. In other words, the SiPM panel 142 can be optically connected to the scintillator 141. Alternatively, the SiPM panel 142 can be directly formed on the scintillator 141. In other words, the SiPM panel 142 can be formed by forming a semiconductor directly on a surface of the scintillator 141.

Moreover, each of the SiPM panels 142 is constituted of an SiPM each serving as a channel. For example, FIG. 2 shows an example in which the SiPM panel 142 covering each face of the scintillator 141 is constituted of 4 (=2×2) SiPMs. However, the number of SiPMs constituting the SiPM panel 142 on each face can be 1 (=1×1), or 32 (=8×4). When the number of SiPM on each face is 4, the total number of output channels of the detector module 140 is 24 (2×2×6). Each SiPM is an example of a photo detector.

The count-data calculating circuitry 143 includes clock circuitry, trigger circuitry, energy integrator circuitry, and input/output circuitry with respect to an external devices, and is electrical circuitry that has a function of processing a signal from the SiPM panel 142 and outputting a processing result to the count-data acquisition circuitry 15 described later.

Figure 3:
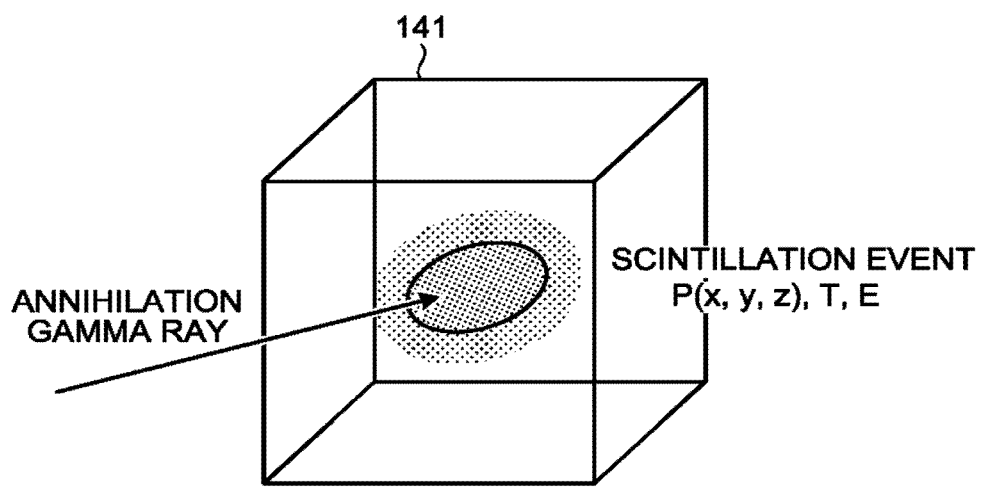
FIG. 3 is a diagram for explaining count-data acquisition circuitry according to the first embodiment.

The count-data acquisition circuitry 15 is electrical circuitry that has a function of acquiring the processing result output by each of the count-data calculating circuitry 143 and calculating count data. The count-data acquisition circuitry 15 is an example of calibration circuitry. FIG. 3 is a diagram for explaining the count-data acquisition circuitry 15 according to the first embodiment.

FIG. 3 shows only the scintillator 141 for convenience' sake. The count-data acquisition circuitry 15 calculates a spatial position (P) and a time of conversion (T), and an energy value (E) of a converted gamma ray when an annihilation gamma ray enters and is converted into scintillation light by the scintillator 141 as shown in FIG. 3, as the count data.

When an annihilation gamma ray enters and is converted into scintillation light as shown in FIG. 3, the count-data acquisition circuitry 15 calculates spatial coordinates (x, y, z) as a spatial position (P) at the conversion to scintillation light. The spatial position (P) at the conversion to scintillation light is also referred to as a scintillation position.

More specifically, the count-data acquisition circuitry 15 calculates the spatial position (P) by calculation of a center of gravity using electrical signals from respective SiPMs (also referred to as channels). For example, the count-data acquisition circuitry 15 identifies plural channels that have converted scintillation light into an electrical signal at the same time. The count-data acquisition circuitry 15 then calculates a position of the center of gravity by using the position of each of the identified channels and the intensity of the electrical signals, to determine the spatial position (P) that indicates a spatial position in the scintillator 141 at which the annihilation gamma ray has entered the scintillator 141.

Furthermore, the count-data acquisition circuitry 15 measures a scintillation time (t) as the detection time (T) at which the annihilation gamma ray has been detected by the SiPM. More specifically, the count-data acquisition circuitry 15 calculates the detection time (T) at which the annihilation gamma ray has been detected by the SiPM based on a distance from the spatial position (p) to the SiPM. For example, the count-data acquisition circuitry 15 determines a time at which an electrical signal is acquired from each channel as a precorrection detection time (T'). More specifically, the count-data acquisition circuitry 15 determines the precorrection detection time (T') at the accuracy of 10 to 12 seconds (picoseconds) unit. The precorrection detection time (T') can be an absolute time that is recorded by the clock circuitry or an elapsed time from a point of time when imaging is started.

The precorrection detection time (T') is a time at which the count-data acquisition circuitry 15 acquires an electrical signal from an SiPM, and is not the detection time (T) at which an annihilation gamma ray is detected by an SiPM. That is, the precorrection detection time (T') is a time delayed from the detection time (T) at which an annihilation gamma ray is detected by the SiPM, by time for scintillation light to travel until it is received by the SiPM. Therefore, the count-data acquisition circuitry 15 corrects the precorrection detection time (T') based on a distance from the spatial position (P) to the SiPM, to calculate the detection time (T). The count-data acquisition circuitry 15 can check with time-digital-converter (TDC) circuitry for higher accuracy in time measurement.

Moreover, the count-data acquisition circuitry 15 measures a total scintillation energy (E) when an annihilation gamma ray is detected by an SiPM, as the energy value (E) of the annihilation gamma ray. More specifically, the count-data acquisition circuitry 15 calculates the energy value (E) based on an attenuation amount from the spatial position (P) to the SiPM. For example, the count-data acquisition circuitry 15 determines a precorrection energy value (E') of an annihilation gamma ray entering the detector module 140 by performing integral calculation of the intensity of an electrical signal that is output from each SiPM.

The precorrection energy value (E') is an integral value of the intensity of an electrical signal when the integral calculation count-data acquisition circuitry 15 acquires the electrical signal from an SiPM, not the energy value (E) of an annihilation gamma ray when the annihilation gamma ray is detected by the SiPM. That is, the precorrection energy value (E') is a value corresponding to the energy value (E) of the annihilation gamma ray when the annihilation gamma ray is detected by the SiPM subjected to attenuation while scintillation light travels until received by the SiPM. Therefore, the count-data acquisition circuitry 15 calculates the energy value (E) by correcting the precorrection energy value (E') based on the attenuation amount while the scintillation light travels from the spatial position (P) to the SiPM.

The count-data acquisition circuitry 15 stores the acquired count data in a data memory 24 described later. Details of processing of calculating the count data by the count-data acquisition circuitry 15 are described later. The time at conversion (T) is also referred to as the detection time (T).

Referring back to FIG. 1, the console 20 accepts an operation of the PET apparatus by an operator, and controls imaging of a PET image and reconstructs the PET image by using the count data acquired by the base 10. As shown in FIG. 1, the console 20 includes an input interface 21, a display 22, the couch control circuitry 23, the data memory 24, simultaneous-count-data generating circuitry 25, image reconstructing circuitry 26, and system control circuitry 27. The respective components included in the console 20 are connected to each other through a bus.

The input interface 21 is a mouse, a keyboard, and the like, that are used to input various kinds of instructions and settings by an operator of the PET apparatus 100, and transfers the various kinds of instructions and settings input thereto to the system control circuitry 27. For example, the input interface 21 is used to input an imaging start instruction. The display 22 is a monitor or the like that is viewed by the operator, and displays a respiration waveform and a PET image of the subject P, and a graphical user interface (GUI) to accept various kinds of instructions and settings from an operator under control of the system control circuitry 27. The couch control circuitry 23 is electrical circuitry that has a function of controlling the couch driver 13.

Figures 4, 5:
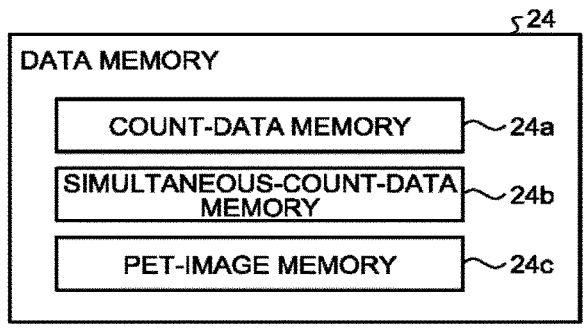
FIG. 4 is a diagram for explaining a data memory according to the first embodiment.
FIG. 5 is a diagram for explaining a list of count data in the first embodiment.

The data memory 24 is electrical circuitry that has a function of storing various kinds of data used in the PET apparatus 100. FIG. 4 is a diagram for explaining the data memory 24 according to the first embodiment. As shown in FIG. 4, the data memory 24 includes a count-data memory 24a, a simultaneous-count-data memory 24b, and a PET-image memory 24c. The data memory 24 is implemented by a semiconductor memory device, such as a random access memory (RAM) and a flash memory, a hard disk, an optical disk, or the like.

The count-data memory 24a is electrical circuitry that has a function of storing a list of count data acquired by the count-data acquisition circuitry 15. Moreover, the list of count data stored in the count-data memory 24a is used in processing by the simultaneous-count-data generating circuitry 25. The list of count data stored in the count-data memory 24a can be deleted, or can be stored for a predetermined period after it is used in the processing by the simultaneous-count-data generating circuitry 25.

FIG. 5 is a diagram for explaining the list of count data in the first embodiment. As shown in FIG. 5, the count-data memory 24a stores count data that includes the spatial position (P), the energy value (E), and the detection time (T) associating with a module identification (ID).

The simultaneous-count-data memory 24b is electrical circuitry that has a function of storing a time-series list of simultaneous count data that is generated by the simultaneous-count-data generating circuitry 25. Furthermore, the time-series list of simultaneous count data stored in the simultaneous-count-data memory 24b is used in processing by the image reconstructing circuitry 26. The time-series list of simultaneous count data stored in the simultaneous-count-data memory 24b can be deleted, or stored for a predetermined period after it is used in the processing by the image reconstructing circuitry 26.

FIG. 6 is a diagram for explaining the time-series list of simultaneous count data in the first embodiment. As shown in FIG. 6, the simultaneous-count-data memory 24b stores sets of count data, associating with a coincidence number (No.), which is a serial number of simultaneous count data. It indicates that a time difference of the detection time (T) of the data stored in a group of the same coincidence No. is within a time window range. That is, the example shown in FIG. 6 indicates that T11 and T22 of coincidence No. 1 are within the time window range, and T12 and T32 of coincidence No. 2 are within the time window range, and T13 and T33 of coincidence No. 3 are within the time window range. In the time-series list of simultaneous count data in the first embodiment, data is arranged in approximately chronological order based on the detection time (T) of the count data.

The PET-image memory 24c is electrical circuitry that has a function of storing a PET image reconstructed by the image reconstructing circuitry 26. Moreover, the PET image stored in the PET-image memory 24c is displayed on the display 22 by the system control circuitry 27.

Referring back to FIG. 1, the simultaneous-count-data generating circuitry 25 is electrical circuitry that has a function of generating time-series list of simultaneous count data by using the list of count data acquired by the count-data acquisition circuitry 15. Specifically, the simultaneous-count-data generating circuitry 25 searches for a set of count data that is acquired when a pair of annihilation gamma rays are counted at approximately the same time from the list of count data stored in the count-data memory 24a based on the detection time (T) of the count data. Moreover, the simultaneous-count-data generating circuitry 25 generates simultaneous count data for each set of the searched count data, and stores the generated simultaneous count data in the simultaneous-count-data memory 24b, arranging in approximately chronological order.

For example, the simultaneous-count-data generating circuitry 25 is electrical circuitry that has a function of generating simultaneous count data based on simultaneous-count-data generation condition input by the operator. In the simultaneous-count-data generation condition, a time window range is specified. For example, the simultaneous-count-data generating circuitry 25 generates the simultaneous count data based on the time window range.

For example, the simultaneous-count-data generating circuitry 25 refers to the count-data memory 24a and searches for a set of count data, a time difference in the detection time (T) of which is within the time window range among the detector modules 140. For example, when having found sets of "P11, E11, T11" and "P22, E22, T22" are a set satisfying the simultaneous-count-data generation condition, the simultaneous-count-data generating circuitry 25 generates simultaneous count data with the sets to store in the simultaneous-count-data memory 24b. The simultaneous-count-data generating circuitry 25 can generate the simultaneous count data by using an energy window range together with the time window range.

The image reconstructing circuitry 26 is electrical circuitry that has a function of reconstructing a PET image. Specifically, the image reconstructing circuitry 26 reads the time-series list of simultaneous count data stored in the simultaneous-count-data memory 24b, and reconstructs a PET image by using the read time-series list. Moreover, the image reconstructing circuitry 26 stores the reconstructed PET image in the PET-image memory 24c.

The system control circuitry 27 is electrical circuitry that has a function of controlling the entire PET apparatus 100 by controlling the base 10 and the console 20. For example, the system control circuitry 27 controls imaging in the PET apparatus 100.

Moreover, the couch control circuitry 23, the simultaneous-count-data generating circuitry 25, the image reconstructing circuitry 26, and the system control circuitry 27, and the like described above are implemented by an integrated circuit, such as an application specific integrated circuit (ASIC) and a field programmable gate array (FPGA), or an electronic circuit, such as a central processing unit (CPU) and a micro processing unit (MPU).

As above, the entire configuration of the PET apparatus 100 according to the first embodiment has been explained. With the configuration, the PET apparatus 100 according to the first embodiment calculates the spatial position (P) and the time (T) when an incident annihilation gamma ray is converted into scintillation light by the scintillator 141, and the energy value (E) of the gamma ray obtained by conversion, as count data. The PET apparatus 100 then generates a time-series list of calculated count data, and reconstructs a PET image by using the time-series list.

To measure a scintillation position and a scintillation time accurately in the PET apparatus 100, measurement of an output power of an SiPM and calibration based on the measured output power are necessary.

In the case of the conventional detectors in which scintillation crystals are assembled in an array, a calibration method is known in which an output power of an individual photon detector is adjusted such that a peak of an output (response function) occurring when the photon detector receives light matches with a scintillation photon in a monochromatic gamma ray scintillator, the energy of which has been known.

However, the calibration method using the conventional monochromatic gamma ray is difficult to be applied to calibration processing of the detector 14 with monolithic scintillators. For example, in the detector 14 with monolithic scintillators, scintillation points are distributed in a wide range. Therefore, an output of each SiPM varies per incidence.

Furthermore, even if an average of outputs of multiple events is used for calibration of the detector 14, the scintillation events can be unbalanced when it is based on gamma rays entering from a specific direction. For example, many scintillation events occur near a surface of a scintillator to which a gamma ray enters as a result of quantum mechanical gamma-ray absorption process or scattering process, and a few scintillation events occur on a surface opposite to the scintillator surface to which the gamma ray enters.

Furthermore, in scintillation near a surface including a scintillator side surface, photons subjected to Compton scattering often escape from the scintillator. In this case, the number of optical photons that enter the detector 14 decreases.

As described above, when a monochromatic gamma ray is entered, it is difficult to cause the scintillation event uniformly at each position in a monolithic scintillator. Therefore, there is a difficulty in performing processing to calibrate the output of the detector 14 based on incidence of a monochromatic gamma ray.

For this reason, the PET apparatus 100 according to the first embodiment calibrates an output of the detector 14 without using a gamma ray entering from outside. More specifically, the PET apparatus 100 according to the first embodiment detects photons of 88 keV, 201 keV, 306 keV, and 400 keV emitted by a radioactive isotope, Lu-176 included in the scintillator 141, and calibrates an electrical signal output from each SiPM.

For example, the plural SiPMs output electrical signals according to a radiation quantity radiated from the self-radioactive scintillator 141. That is, the SiPMs output electrical signals according to the number of scintillation photons generated by radiation from the self-radioactive scintillator 141. The count-data acquisition circuitry 15 calibrates an electrical signal output from each SiPM such that results of calculation based on the electrical signals output from the respective SiPMs are the same. In the following details of the calibration processing by the count-data acquisition circuitry 15 are explained.

Figure 7:
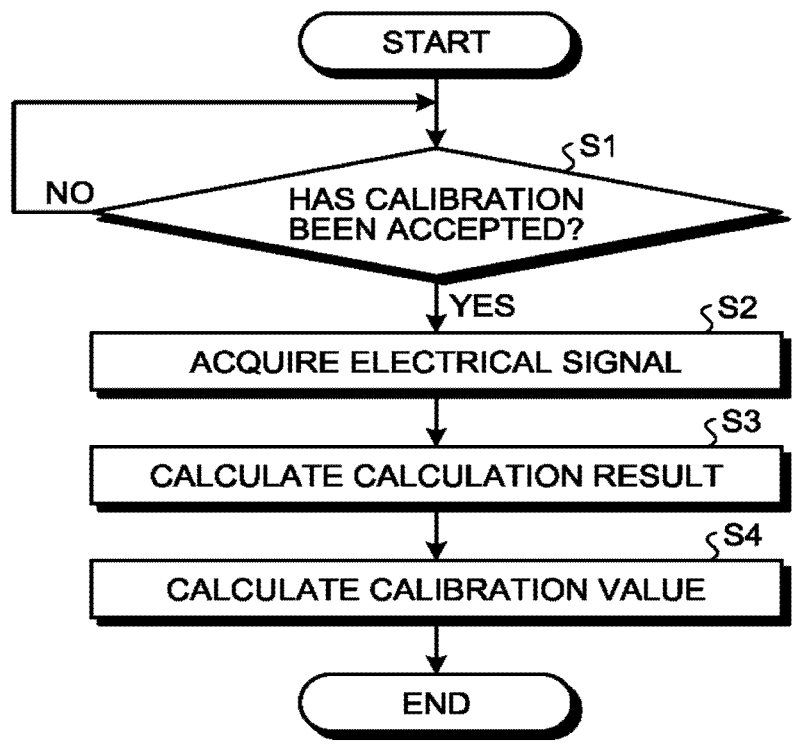
FIG. 7 is a flowchart showing a procedure of calibration processing performed by the count-data acquisition circuitry according to the first embodiment.

FIG. 7 is a flowchart showing a procedure of the calibration processing performed by the count-data acquisition circuitry 15 according to the first embodiment. In FIG. 7, to which step each component corresponds is explained. Step 1 to Step S4 are steps implemented by the count-data acquisition circuitry 15. The calibration processing shown in FIG. 7 is performed between imaging of the subject P by the PET apparatus 100.

At step S1, the count-data acquisition circuitry 15 determines whether start of calibration has been accepted. When it is not determined that start of calibration has not been accepted (step S1: NO), the count-data acquisition circuitry 15 repeats the determination processing at step S1. On the other hand, when it is determined that start of calibration has been accepted (step S1: YES), the count-data acquisition circuitry 15 proceeds to step S2.

At step S2, the count-data acquisition circuitry 15 acquires electrical signals. For example, each SiPM of each o the detector modules 140 outputs an electrical signal according to a quantity of radiation radiated from the self-radioactive scintillator 141 to the count-data calculating circuitry 143 of each of the detector modules 140. The count-data acquisition circuitry 15 acquires an electrical signal output from each SiPM from the count-data calculating circuitry 143 of each of the detector modules 140.

Figure 8:
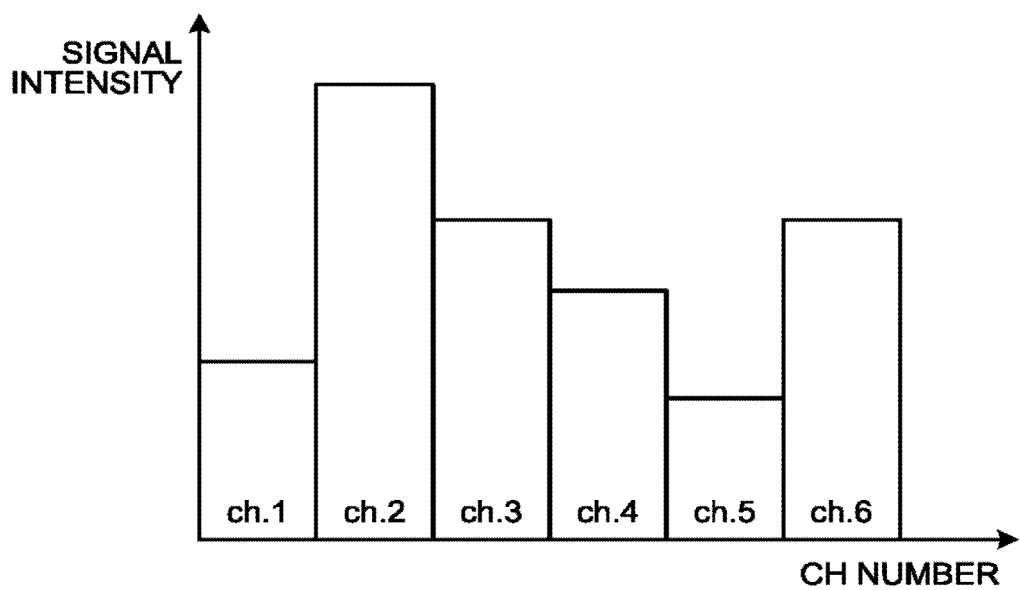
FIG. 8 is a diagram for explaining the first embodiment.

At step S3, the count-data acquisition circuitry 15 calculates a calculation result. For example, the count-data acquisition circuitry 15 generates a histogram that indicates the intensity of signal of each channel by using the electrical signal from the SiPM included in each of the SiPM panel 142. In other words, the count-data acquisition circuitry 15 handles a count value of the electrical signals output from the respective SiPM as the calculation result. FIG. 8 is a diagram for explaining the first embodiment.

A horizontal axis in FIG. 8 is for a channel number, and a vertical axis in FIG. 8 is for a signal intensity of each channel. The example in FIG. 8 shows a case in which the number of SiPM of each face constituting the SiPM panel 142 is one, and the number of channels is six. Moreover, the example in FIG. 8 shows signal intensities of channel number 1 (ch. 1) to channel number 6 (ch. 6) from the left side of the horizontal axis sequentially. Furthermore, in the example in FIG. 8, a signal intensity in the vertical axis is a value acquired by subjecting the intensity of an electrical signal of each SiPM to integral calculation. The count-data acquisition circuitry 15 generates a histogram as shown in FIG. 8 for each light emission event.

In the example shown in FIG. 8, the count-data acquisition circuitry 15 calculates the signal intensity of channel number 1 as α2, the signal intensity of channel number 2 as α5, and the signal intensity of channel number 3 as α4. Moreover, the signal intensity of channel number 2 as α5 calculates the signal intensity of channel number 4 as α3, the signal intensity of channel number 5 as α1, and the signal intensity of channel number 6 as α4. In the example shown in FIG. 8, the magnitude relationship of the signal intensities in the example shown in FIG. 8 is α1<α2<α3<α4<α5.

Figure 9:
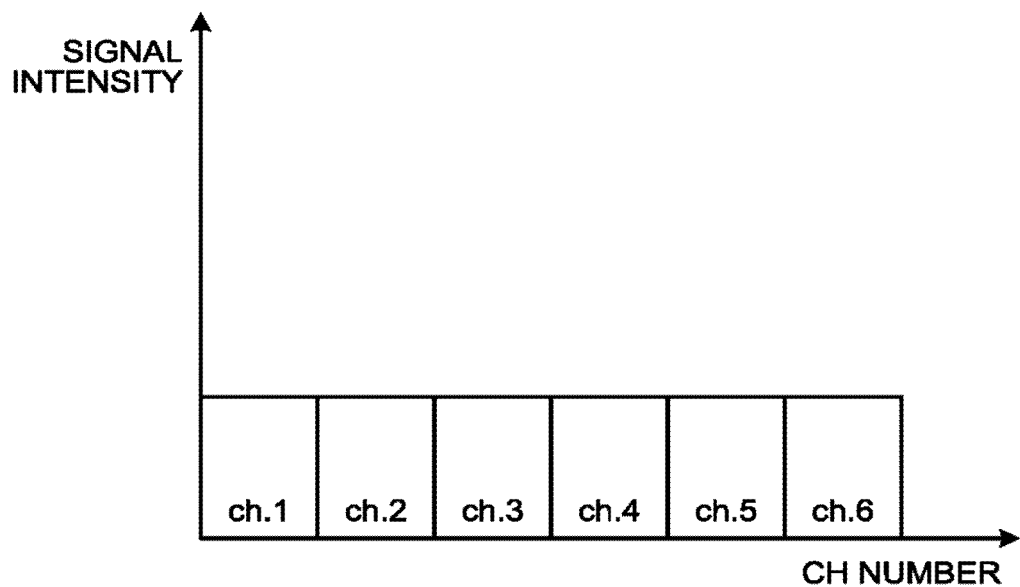
FIG. 9 is a diagram for explaining the first embodiment.

Referring back to FIG. 7, at step S4, the count-data acquisition circuitry 15 calculates a calibration value. For example, the count-data acquisition circuitry 15 calculates the calibration value such that results of calculation based on electrical signals output from the respective SiPMs are equal to each other among the SiPMs. FIG. 9 is a diagram for explaining the first embodiment.

FIG. 9 shows a histogram when the number of channels is six similarly to the case of FIG. 8. The count-data acquisition circuitry 15 calibrates an electrical signal that is output from each SiPM by using the positional relationship between a region in each SiPM and the scintillator 141. For example, the count-data acquisition circuitry 15 calculates, per SiPM, a weight proportional to a reciprocal of a calculation value in each SiPM as the calibration value as shown in FIG. 9. In the example shown in FIG. 9, the count-data acquisition circuitry 15 calculates weight proportional to a reciprocal of the signal intensity shown in FIG. 8 as the calibration value.

As an example, the count-data acquisition circuitry 15 calculates a calibration value of channel 1 as 1/α2, the calibration value of channel 2 as 1/α5, the calibration value of channel 3 as 1/α4. Furthermore, the count-data acquisition circuitry 15 calculates the calibration value of channel 4 as 1/α3, the calibration value of channel 5 as 1/α1, and the calibration value of channel 6 as 1/α4. The count-data acquisition circuitry 15 stores the calculated calibration values, associating with the SiPMs of the respective detector modules 140.

Figure 10:
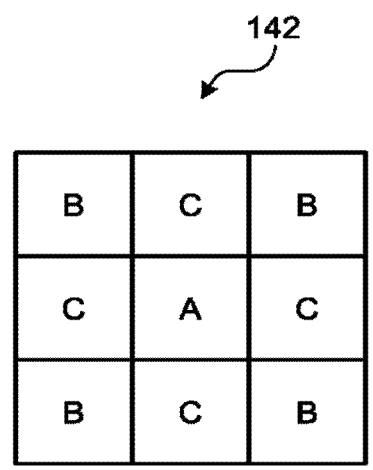
FIG. 10 is a diagram for explaining the first embodiment.

Although the case in which the number of SiPMs on each face constituting the SiPM panel 142 is one and the number of channels is six has been explained in the examples using FIG. 7 and FIG. 9, embodiments are not limited thereto. For example, the embodiment described above is also applicable to a case in which the number of SiPMs on each face constituting the SiPM panel 142 is two or more. In this case also, the count-data acquisition circuitry 15 calibrates an electrical signal output from each SiPM by using the positional relationship between a region in each SiPM and the scintillator 141. FIG. 10 is a diagram for explaining the first embodiment.

In FIG. 10, a case in which the number of SiPMs on each face constituting the SiPM panel 142 is 9 (3×3), and the number of channels is 54 is explained. As shown in FIG. 10, the respective SiPMs included in the SiPM panel 142 are categorized into type A, type B, and type C based on a positional relationship with respect to the center of the scintillator 141. In this example, the detector module 140 includes six pieces of type A SiPMs, 24 pieces of type B SiPMs, and 24 pieces of type C SiPMs.

The count-data acquisition circuitry 15 calibrates an electrical signal output from each SiPM to be same among the type A SiPMs. Moreover, the count-data acquisition circuitry 15 calibrates an electrical signal output from each SiPM to be same among the type B SiPMs. Similarly, the count-data acquisition circuitry 15 calibrates an electrical signal output from each SiPM to be same among the type C SiPMs in the detector module 140.

Figure 11:
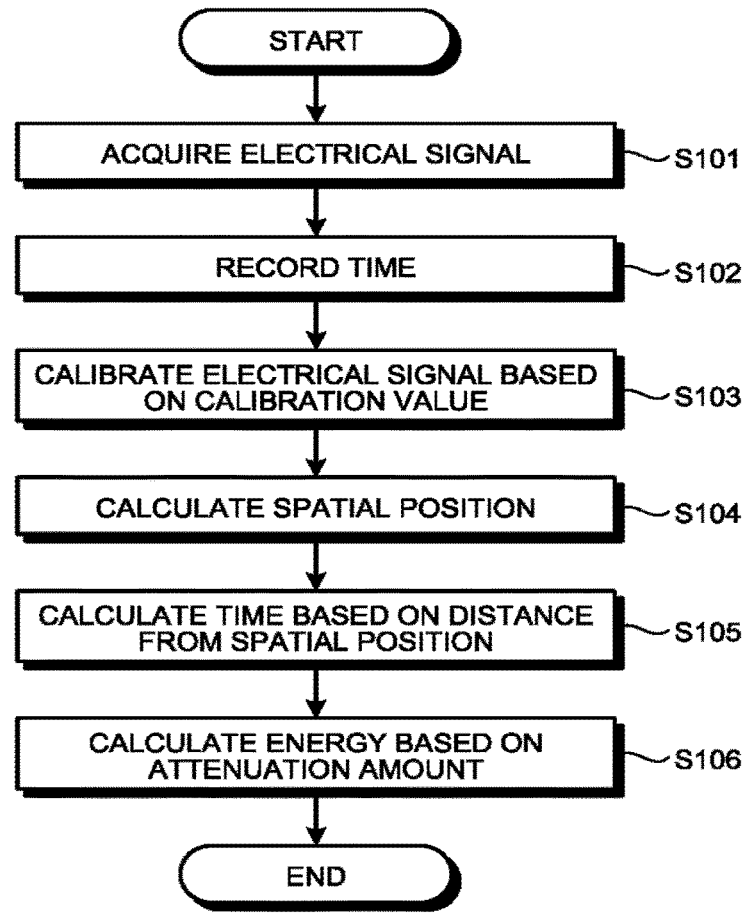
FIG. 11 is a flowchart showing a procedure of count-data calculation processing performed by the count-data acquisition circuitry according to the first embodiment.

Subsequently, count-data calculation processing performed the count-data acquisition circuitry 15 is explained. FIG. 11 is a flowchart showing a procedure of the count-data calculation processing performed by the count-data acquisition circuitry 15 according to the first embodiment. In FIG. 11, to which step of the flowchart the respective components correspond is explained. Step S101 to step S106 are steps implemented by the count-data acquisition circuitry 15. The count-data calculation processing shown in FIG. 11 is performed at imaging of the subject P by the PET apparatus 100.

At step S101, the count-data acquisition circuitry 15 acquires an electrical signal. For example, the count-data acquisition circuitry 15 acquires an electrical signal output from an SiPM included in each of the SiPM panels 142 from the count-data calculating circuitry 143. At step S102, the count-data acquisition circuitry 15 records a time at which the electrical signal is acquired.

At step S103, the count-data acquisition circuitry 15 calibrates the electrical signal based on the calibration value. For example, the count-data acquisition circuitry 15 calibrates an electrical signal output from each SiPM such that calculation results based on the electrical signal output from each SiPM are equal to each other among plural SiPMs. More specifically, the count-data acquisition circuitry 15 calibrates the electrical signal output from each SiPM by multiplying a weight proportional to a reciprocal of a count value in each SiPM per multiple SiPMs.

At step S104, the count-data acquisition circuitry 15 calculates a spatial position. The count-data acquisition circuitry 15 calculates spatial coordinates (x, y, z) as the spatial position (P) at the time of conversion to scintillation light.

At step S105, the count-data acquisition circuitry 15 calculates time based on a distance from the spatial position. For example, the count-data acquisition circuitry 15 determines a time at which an electrical signal is acquired from each channel as the detection time (T') based on an absolute time recorded by the clock circuitry. The count-data acquisition circuitry 15 then calculates a time (T) at the time of conversion to scintillation light by correcting the detection time (T') based on a distance from the spatial position (P) to the SiPM. Subsequently, the count-data acquisition circuitry 15 further corrects the time (T) at the time of conversion to scintillation light based on the spatial position (P) and a refractivity of the scintillator 141.

At step S106, the count-data acquisition circuitry 15 calculates an energy value based on an attenuation amount. For example, the count-data acquisition circuitry 15 determines the precorrection energy value (E') of an annihilation gamma ray entering to the detector module 140 by performing integral calculation of an intensity of an electrical signal output from each SiPM. The count-data acquisition circuitry 15 then calculates the energy value (E) by correcting the precorrection energy value (E') based on the attenuation amount while the scintillation light travels from the spatial position (P) to the SiPM.

Thus, the simultaneous-count-data generating circuitry 25 generates a time-series list of simultaneous count data by using a list of count data acquired by the count-data acquisition circuitry 15. Subsequently, the image reconstructing circuitry 26 reads the time-series list of simultaneous count data stored in the simultaneous-count-data memory 24b, and reconstructs a PET image by using the read time-series list.

As described above, in the PET apparatus 100 according to the first embodiment, an electrical signal output from each SiPM is calibrated such that calculation results based on the electrical signal according to a quantity of radiation radiated from the self-radioactive scintillator 141 are to be same among multiple SiPMs. Thus, according to the first embodiment, an output of the detector 14 using a monolithic scintillator can be calibrated without using an external gamma ray source.

Furthermore, in the calibration processing using an external gamma ray source, it is difficult to obtain uniform scintillation events at respective positions of the detector 14, and the scintillation events are unbalanced. However, in the PET apparatus 100 according to the first embodiment, the calibration processing is performed based on an electrical signal according to the self-radioactivity. This self-radioactivity is assumed to be obtained at respective positions in the detector 14 uniformly. Therefore, according to the PET apparatus 100 according to the first embodiment, it is possible to improve the calibration accuracy from that of the calibration processing using an external gamma ray source.

Moreover, in the PET apparatus 100 according to the first embodiment, any special device is not necessary to perform the calibration processing, and the calibration processing can be performed individually per detector. Therefore, detectors that has been calibrated in parallel to a manufacturing process can be prepared. Furthermore, the calibration processing can always be performed as a service part.

Moreover, when the calibration processing based on the self-radioactivity is performed in a case in which a detector having multiple scintillator crystals in small sizes assembled in an array is used, the number of events acquired per scintillator is small and, therefore, an output of the detector 14 cannot be calibrated. On the other hand, when the scintillator 141 is constituted of a single crystal, the size of the scintillator 141 is large and, therefore, the radiation quantity radiated therefrom is large. Accordingly, the PET apparatus 100 according to the first embodiment can obtain the sufficient number of events by being equipped with the scintillator 141 constituted of a single crystal even when the calibration processing is performed based on the self-radioactivity, and enables the calibration processing of an output of the detector 14.

The scintillator included in the PET apparatus 100 is not limited to the scintillator 141 constituted of a single crystal. That is, as long as it is a scintillator with which the quantity of radiation radiated by the self-radioactivity is large, and is a scintillator enabled to obtain the sufficient number of events, the scintillator is not required to be of monolithic. For example, when a detector in which multiple scintillator crystals are assembled in an array is used, if the size of each scintillator crystal is large enough, the PET apparatus 100 can calibrate an output of the detector based on the quantity of radiation radiated from each self-radioactive scintillator crystal.

For example, the PET apparatus 100 includes multiple scintillators and multiple SiPMs. The SiPMs output electrical signals according to a quantity of radiation radiated from the self-radioactive scintillator. An SiPM can be provided per scintillator, or an SIPM can be provided per plural scintillators, or more than one SiPMs can be provided to a single scintillator. When a sufficient quantity of radiation is emitted from each of the scintillators, the can calibrates the electrical signals output from the respective SiPMs such that calibration results based on the electrical signals output from the respective SiPMs are same among the SiPMs. The PET apparatus 100 can be equipped with a photomultiplier tube (PMT) instead of SiPM.

Furthermore, the count-data acquisition circuitry 15 can perform various kinds of calibration processing based on the self-radioactivity, in addition to the calibration processing for an output of the detector 14.

For example, the count-data acquisition circuitry 15 can perform timing calibration based on a quantity of radiation radiated from the scintillator 141. For example, time required for the count-data calculating circuitry 143 to acquire an electrical signal from the SiPM panel 142 after the SiPM panel 142 outputs an electrical signal based on scintillation light varies due to individual differences of the SiPM panels 142. Therefore, the count-data acquisition circuitry 15 can perform timing calibration such that time required for the count-data calculating circuitry 143 to acquire an electrical signal that is output by the SiPM panel 142 according to the self-radioactivity is to be same among the plural SiPM panels 142.

Moreover, for example, the count-data acquisition circuitry 15 can perform offset correction relating to signal amplification processing. For example, each of the SiPM panels 142 outputs an electrical signal based on scintillation light after subjecting it to amplification by an operational amplifier to the count-data calculating circuitry 143. When the electrical signal (an input voltage to the operational amplifier) based on scintillation light is smaller than an offset value, there is a case that an output voltage from the operational amplifier cannot be obtained. That is, when the input voltage to the operational amplifier is equal to or smaller than the offset value, the output voltage from the operational amplifier is to be 0. Furthermore, variations occur in the offset value due to individual differences of operational amplifiers. Therefore, the count-data acquisition circuitry 15 can acquire an offset value of each operational amplifier according to whether an electrical signal output by the SiPM panel 142 according to the self-radioactivity appears as an output voltage from the operational amplifier.

The timing calibration and the offset correction relating to signal amplification processing can be performed also when a quantity of radiation radiated from a scintillator is small. That is, in the timing calibration and the offset correction, it is enough if detection of an event of output of an electrical signal by an SiPM is possible, and information about the magnitude of the electrical signal is not necessary. Therefore, even when a quantity of radiation radiated from each scintillator is small in a case of using a detector in which multiple small-sized scintillator crystals are assembled in an array or the like, the timing calibration and the offset correction are possible. In other words, the PET apparatus 100 according to the first embodiment is enabled to perform the calibration processing for an output of the detector 14, in addition to the timing calibration and the offset correction, by having a scintillator (monolithic scintillator, or the like), a radiation quantity of which is large.

Figure 12:
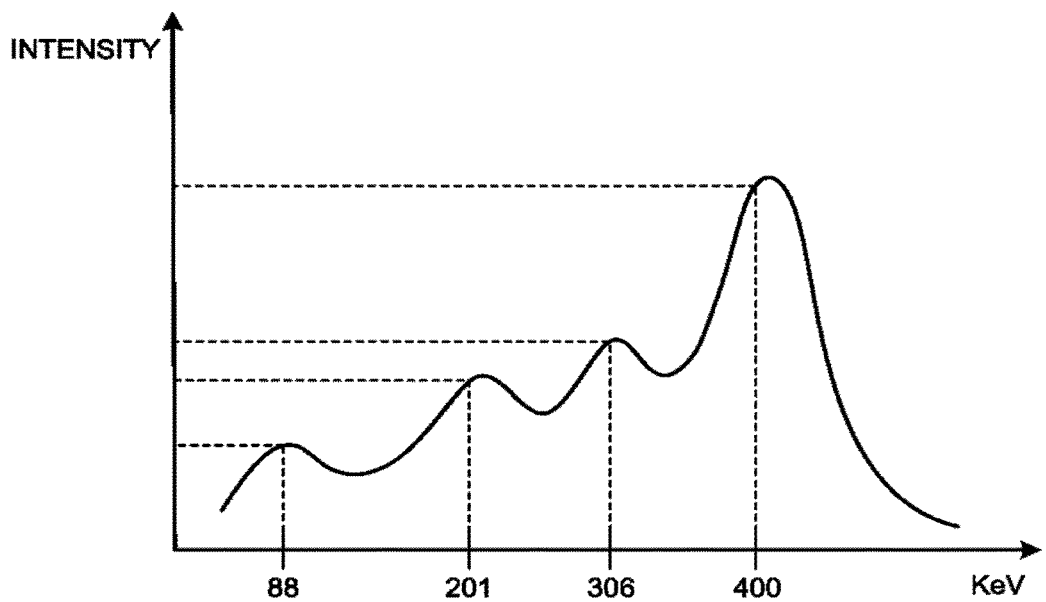
FIG. 12 is a diagram for explaining a modification of the first embodiment.

Although the count-data acquisition circuitry 15 has been explained to use a count value of an electrical signal output from each SiPM as a calculation result in the above embodiment, embodiments are not limited thereto. For example, the count-data acquisition circuitry 15 can use a spectrum generated by using an electrical signal output from each SiPM as a calculation result. FIG. 12 is a diagram for explaining a modification of the first embodiment.

In FIG. 12, a horizontal axis is for an energy value, and a vertical axis is for an intensity. For example, the count-data acquisition circuitry 15 detects photons of 88 keV, 201 keV, 306 keV, and 400 keV emitted by a radioactive isotope, Lu-176, and generates a spectrum as shown in FIG. 12 for each SiPM. The count-data acquisition circuitry 15 calculates a calibration value such that spectrums are same among multiple SiPMs. For example, the count-data acquisition circuitry 15 calculates an amplification factor with which spectrums become same, as a calibration value. The count-data acquisition circuitry 15 calibrates an electrical signal output from each SiPM by adjusting the amplification factor of the respective SiPMs based on the spectrums.

Embodiments are not limited to the embodiment described above.

Moreover, although explanation has been given, assuming that Lu-176 included in the scintillator 141 in each of the detector modules 140 is the same, the embodiment described above is applicable also to a case in which Lu-176 included in the scintillators 141 varies among scintillators. In this case, for example, the count-data acquisition circuitry 15 calibrates an electrical signal output from the SiPMs in the respective detector modules 140 by dividing a count value of each of the SiPMs in the respective detector modules 140 by a count value per unit time in each of the detector modules 140.

Although it has been explained that the calibration processing is performed between imaging of the subject P by the PET apparatus 100 in the embodiment described above, embodiments are not limited thereto. For example, the calibration processing can be performed during operation of the PET apparatus 100. That is, the count-data acquisition circuitry 15 calibrates an electrical signal that is output from each SiPM during imaging of the subject P by the PET apparatus 100.

Although it has been explained that the detector module 140 includes the count-data calculating circuitry 143 in the embodiment described above, embodiments are not limited thereto. For example, the count-data calculating circuitry 143 can be provided independently of the detector module 140. Furthermore, the multiple detector modules 140 can be divided into blocks, and each block can include the count-data calculating circuitry 143.

Moreover, although it has been explained that the count-data calculating circuitry 143 outputs a signal from the SiPM panel 142 to the count-data acquisition circuitry 15, and the count-data acquisition circuitry 15 processes the signal from the SiPM panel 142 in the embodiment described above, embodiments are not limited thereto. For example, the count-data acquisition circuitry 15 can acquire a signal processing result output from the count-data calculating circuitry 143. In this case, the count-data calculating circuitry 143 acquires a signal from each of the SiPM panels 142, and generates an intensity distribution that indicates the intensity of an electrical signal output by each SiPM. Alternatively, the count-data calculating circuitry 143 acquires a signal from each of the SiPM panel 142 and generates a spectrum of each SiPM.

Furthermore, although it has been explained that the scintillator 141 has a hexahedral shape in the embodiment described above, embodiments are not limited thereto. For example, the scintillator 141 can have a spherical shape. In this case, the SiPM panels 142 are arranged along the spherical shape of the scintillator 141. Alternatively, for example, the scintillator 141 in a spherical shape can be formed into a hexahedron shape by using a light guide to fill space, and be equipped with plural SiPM panels 142 on at least two faces of the scintillator 141.

Although the PET apparatus 100 has been explained as an example of a medical image diagnosis apparatus in the embodiment described above, embodiments are not limited thereto. For example, the medical image diagnosis apparatus can be a single photon emission computed tomography (SPECT). Moreover, the medical image diagnosis apparatus can be an X-ray computed tomography (CT) apparatus or an X-ray diagnosis apparatus. The PET apparatus 100 can be for mammography.

The term "processor" used in the above explanation signifies, for example, a CPU, a graphics processing unit (GPU), or a circuit such as an ASIC, a programmable logic device (for example, simple programmable logic device (SPLD), complex programmable logic device (CPLD)), and an FPGA. The processor reads and executes a program stored in a memory, and thereby implements a function. Instead of storing a program in the memory, the program can be directly installed in a circuit of the processor. In this case, the processor reads and executes the program installed in the circuit of the processor to implement the function. The respective processors in the present embodiment are not limited to be structured as an independent circuit per processor, but can be structured by combining multiple independent processors to form a single processor to implement the functions. Furthermore, more than one component in FIG. 1 can be integrated to a single processor to implement the functions.

The respective components of the respective devices illustrated in the explanation of the embodiment described above are of functional concept, and it is not necessarily required to be configured physically as illustrated. That is, specific forms of distribution and integration of the respective devices are not limited to the ones illustrated, and all or a part thereof can be configured to be distributed or integrated functionally or physically in arbitrary units according to various kinds of loads, usage conditions, and the like. Furthermore, as for the respective processing functions performed by the respective devices, all or an arbitrary part thereof can be implemented by a CPU and a computer program that is analyzed and executed by the CPU, or can be implemented as hardware by wired logic.

Furthermore, the control method explained in the above embodiment can be implemented by executing a control program that has been prepared in advance by a computer such as a personal computer and a workstation. This control program can be distributed through a network such as the Internet. Furthermore, this control program can be stored in a computer-readable recording medium, such as a hard disk, a flexible disk (FD), a compact-disk read-only memory (CD-ROM), a magneto optical disk (MO), and a digital versatile disk (DVD), and can be executed by being read by a computer from the recording medium.

According to at least one of the embodiments explained above, a detector including a scintillator can be calibrated easily.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus, comprising:
a self-radioactive scintillator constituted of a single crystal;
a plurality of photon detectors that are arranged at a plurality of different positions in the scintillator, each photon detector of the plurality of photon detectors configured to output a corresponding electrical signal according to a corresponding quantity of radiation radiated from the scintillator and received by the photon detector; and
calibration circuitry configured to calibrate each corresponding electrical signal output from each photon detector of the plurality of photon detectors such that calculation results based on the corresponding electrical signal output from each photon detector of the plurality of photon detectors are identical among the plurality of photon detectors.

2. The medical image diagnosis apparatus according to claim 1, wherein the calibration circuitry is further configured to calibrate the corresponding electrical signal output from each photon detector of the plurality of photon detectors by using a positional relationship between a region in the photon detector and the scintillator.

3. The medical image diagnosis apparatus according to claim 1, wherein the calibration circuitry is further configured to use a count value of the corresponding electrical signal output from each photon detector of the plurality of photon detectors as the calculation result.

4. The medical image diagnosis apparatus according to claim 3, wherein the calibration circuitry is further configured to calibrate the corresponding electrical signal output from each photon detector of the plurality of photon detectors by, for each photon detector, multiplying a weight proportional to a reciprocal of the count value in the photon detector.

5. The medical image diagnosis apparatus according to claim 1, wherein
the medical image diagnosis apparatus further comprises a plurality of detector modules that include the scintillator and the plurality of photon detectors, and
the calibration circuitry is further configured to calibrate the corresponding electrical signal output from each photon detector in each of the detector modules by dividing a count value per photon detector in each of the detector modules by a count value per unit time in each of the detector modules.

6. The medical image diagnosis apparatus according to claim 1, wherein the calibration circuitry is further configured to use a spectrum that is generated by using the corresponding electrical signal output from each photon detector of the plurality of photon detectors.

7. The medical image diagnosis apparatus according to claim 6, wherein the calibration circuitry is further configured to calibrate the corresponding electrical signal output from each photon detector of the plurality of photon detectors by adjusting an amplification factor of each photon detector of the plurality of photon detectors, based on the spectrum.

8. The medical image diagnosis apparatus according to claim 1, wherein the calibration circuitry is further configured to calibrate the corresponding electrical signal output from each photon detector of the plurality of photon detectors during imaging of a subject by the medical image diagnosis apparatus.

9. A medical image diagnosis apparatus, comprising:
a plurality of self-radioactive scintillators;
a plurality of photon detectors that are arranged in the scintillators in plurality, and that output an electrical signal according to a quantity of radiation radiated by a scintillator and received by the photon detectors; and
calibration circuitry configured to calibrate each corresponding electrical signal output from each photon detector of the plurality of photon detectors such that calculation results based on the corresponding electrical signal output from each photon detector of the plurality of photon detectors are identical among the plurality of photon detectors.

* * * * *